(12) United States Patent
Hols et al.

(10) Patent No.: US 6,627,420 B1
(45) Date of Patent: Sep. 30, 2003

(54) PROCESS FOR THE PRODUCTION OF ALANINE BY RECOMBINANT MICROORGANISMS

(75) Inventors: Pascal Hols, Vedrin (BE); Michiel Kleerebezem, Ede (NL); Oscar Paul Kuipers, Ede (NL); Thierry Ferain, Naast (BE); Jean Marcelin Alain Marie Ghislain Delcour, Walhain (BE); Willem Meindert De Vos, Bennekom (NL)

(73) Assignee: Nederlands Instituut voor Zuivelonderzoek, Ede (NL)

( * ) Notice: Subject to any disclaimer, the term of this patent is extended or adjusted under 35 U.S.C. 154(b) by 0 days.

(21) Appl. No.: 09/600,449

(22) PCT Filed: Jan. 15, 1999

(86) PCT No.: PCT/NL99/00021

§ 371 (c)(1),
(2), (4) Date: Nov. 30, 2000

(87) PCT Pub. No.: WO99/36556

PCT Pub. Date: Jul. 22, 1999

(30) Foreign Application Priority Data

Jan. 16, 1998 (NL) ............................................ 1008054

(51) Int. Cl.[7] ................................................ C12P 13/06
(52) U.S. Cl. ...................................................... 435/116
(58) Field of Search ................................. 435/116, 106

(56) References Cited

FOREIGN PATENT DOCUMENTS

EP 0 567 644 11/1993
EP 0 603 865 6/1994

OTHER PUBLICATIONS

Orlygsson et al., "Alanine as an end product during fermentation of monosaccharides by Clostridium strain P2", *Antonie Van Leeuwenhoek*, vol. 68, No. 4, pp. 273–280, (1995).

Ferain et al., "Knockout of the Two idh Genes Has a Major Impact on Peptidoglycan Precursor Synthesis in Lactobacillus plantarum" *Journal of Bacteriology*, vol. 178, No. 18, pp. 5431–5437, (1996).

Galkin et al., "Synthesis of Optically Active Amino Acids from α–Keto Acids with *Escherichia coli* Cells Expressing Heterologous Genes", *Applied and Environmental Microbiology* vol. 63, No. 12, pp. 4651–4656, (1997).

Patent Abstracts of Japan, Publication No. 62036196, Publication Date Feb. 17, 1987.

*Primary Examiner*—Ponnathapu Achutamurthy
*Assistant Examiner*—Kathleen Kerr
(74) *Attorney, Agent, or Firm*—Browdy and Neimark (57) ABSTRACT

A process for preparing alanine by culturing a genetically modified microorganism that produces alanine from glucose. The microorganism is one that has been modified to result in an overexpression of an endogenous alanine dehydrogenase gene, expression of a heterologous alanine dehydrogenase gene, or a combination of both. The source of alanine dehydrogenase may be *Bacillus sphaericus*. The modified microorganisms may be a homofermentative microorganism, such as a strain of *L. lactis*. The process can be used for in situ and stereoscopic preparation of alanine. The invention also relates to the microorganisms and the recombinant DNA molecules that can be used in the invention, as well as to alanine and alanine-containing products obtained according to the process of the invention.

5 Claims, 10 Drawing Sheets fig-1 fig-3a fig-3b fig-3c fig-3d fig-4a fig-4b fig-6a

ALANINE PRODUCTION FROM L. PLANTARUM NCB (nisRK)[pNZalaD] STEADY STATE CELLS/100mM KNaPO4 pH7.5/100mM (NH4+)2SO4/10mM GLUCOSE fig-6b ALANINE PRODUCTION FROM L. PLANTARUM NCB (nisRK)[pNZalaD] STEADY STATE CELLS/KNaPO4 pH7.5/100mM (NH4+ 2SO4/10mM GLUCOSE

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
cgaggatccg gccggttgag gtttctaaag cgg                33

<210> SEQ ID NO 2
<211> LENGTH: 36
<212> TYPE: DNA
<213> ORGANISM: Artificial Sequence -continued

```
<220> FEATURE:
<223> OTHER INFORMATION: Primer

<400> SEQUENCE: 2
cgcgagctca cttgtttcat aagttgcacc gtaacc                                   36
```

PROCESS FOR THE PRODUCTION OF ALANINE BY RECOMBINANT MICROORGANISMS

CROSS REFERENCE TO RELATED APPLICATION

The present application is the national stage under 35 U.S.C. 371 of PCT/NL99/00021, filed Jan. 15, 1999.

The present invention relates to a process for preparing alanine, especially L-alanine, by culturing a genetically modified microorganism that is able to produce alanine from a carbon source.

A process of this type is already known from Uhlenbusch et at., Appl. Environ. Microbiol. 57: 1360–1366 (1991). In this process, L-alanine is produced by culturing a microorganism (Zymomonas mobilis) that has been genetically modified in such a manner that it expresses an alanine dehydrogenase gene. The expressed alanine dehydrogenase converts the glucose in the medium, via conversion into pyruvate, into a mixture of alanine and ethanol, with a maximum alanine yield of 16%, calculated on the amount of glucose converted.

However, Zymomonas mobilis is not a food-grade organism. Nor is Zymomonas mobilis a homofermentative organism, since it forms one molecule of $CO_2$ for each molecule of ethanol produced so that it forms 66% of ethanol and 33% of $CO_2$, calculated on the carbon balance.

L-alanine is used in pharmaceutical and veterinary applications. For example, it is included, together with other amino acids, in preparations for parenteral administration as clinical preoperative and postoperative foods, as well as an animal feed supplement. Furthermore, alanine is used as a food additive on account of its sweet taste.

L-alanine is produced industrially by the decarboxylation of L-aspartate by means of immobilized cells or cell suspensions of Pseudomonas dacunhae. The L-alanine yield may, in this case, exceed 90%, starting from aspartic acid, but this is an expensive substrate.

D/L-alanine can also be prepared by chemical synthesis or by the direct fermentation of sugars. The microorganisms involved in this fermentation, such as Corynebacterium gelatinosium, Arthrobacter oxydans, Brevibacterium lactofermentum, Clostridium sp. and Pyrococcus furiosus, produce D/L-alanine with a maximum conversion rate of 50 to 60%, probably via catalysis by an endogenous alanine dehydrogenase.

EP 0 603 865 describes a process for the production of alanine, in which a microorganism of the genus Escherichia, Cornyebacterium or Brevibacterium, provided with a heterologous L-alanine dehydrogenase activity (for example from Arthrobacter), is used.

None of these microorganisms belongs to the lactic acid bacteria. However, a number of above-mentioned Brevibacterium-strains—such as B.lactofermentum and B.flavum—are classified as among the "food grade" microorganisms. However, this is because they are isolated from food products; they are not applied in the (fermentative) preparation of foodstuffs.

Finally—as far as can be derived from the data given—according to Example 7 of EP 0 603 865 only a maximum conversion of 30% is reached, calculated on the amount of glucose in the medium.

EP 0 567 644 describes a process for the preparation of L-alanine by fermentation using an Arthrobacter-strain. In doing so—as far as can be derived from the data given—according to Example 5 a maximal conversion of 30% is reached, calculated on the amount of glucose in the medium.

However, the Arthrobacter-strains used are not homofermentative and do not belong to the food grade or lactic acid bacteria. Furthermore, according to EP 0 603 865 page 5, lines 1–4 the use of Arthrobacter leads to contamination with "odor producing materials".

J. Oerlgysson et al., Anthonie van Leeuwenhoek, 68 no.4, p. 273–280 (1995) describe the production of alanine using a Clostridium-strain. As far as can be derived from the data given the maximal conversion reached in this case is always less than 50%, calculated on the amount of glucose in the medium. Furthermore, Clostridium is homo-fermentative and does not belong to the food grade- or lactic acid bacteria. Also, on p. 279 it is mentioned that "Clostridium P2 produced almost no alanine from pyruvate, and, in fact, could not grow on pyruvate".

The use of E.coli-strains in the production of alanine is described in A. Galkin et al., Appl. Environ. Microbiology, 1997, p.4651–4656, and in Patent Abstracts of Japan, vol. 11, no.222 (C-435), corresponding to JP-A-62936196. However, E.coli is a hetero-fermentative organism (especially when cultured under minimum $O_2$ conditions) and not a food grade- or lactic acid bacterium.

T. Ferain et al., J. of Bacteriology 1996, p. 5431–5437, describe a L.plantarum-strain (LDH), of which the two genes encoding the native lactate dehydrogenase are disrupted.

However, this reference does not describe the re-routing of the carbon/pyruvate metabolism in this organism towards the formation of alanine; therefore the LDH⁻-mutants can not be applied in the production of alanine.

The aim of the invention is to provide an improved process for the production of alanine, especially L-alanine.

It has now been found that a process of this type can be provided by replacing, in a suitable microorganism, the native metabolic conversion or conversions of sugars into their derivatives (such as lactate) by the formation of alanine, especially L-alanine.

The invention therefore relates to a process for preparing alanine, especially L-alanine, by culturing a genetically modified microorganism that is able to produce alanine from a suitable carbon source in the medium, characterized in that the microorganism used is one whose native sugar metabolism has been diverted to alanine formation, especially L-alanine formation, in such a manner that essentially more than 20%, preferably more than 40%, more preferably more than 60% and most preferably more than 75% of the carbon consumed from the medium is converted into alanine.

According to the invention preferably food grade- and/or lactic acid bacteria are applied and more preferably food grade strains of lactic acid bacteria. However, the invention is not limited to this:

when in the process of the invention a lactic acid bacterium is used (including the preferred food grade lactic acid bacteria), according to the invention essentially more than 20%, preferably more than 40%, more preferably more than 60% and most preferably more than 75% of the carbon consumed from the medium is converted into alanine;

when a food grade microorganism is used that does not belong to the lactic acid bacteria, according to the invention essentially more than 40%, preferably more than 60% and more preferably more than 75% of the carbon consumed from the medium is converted into alanine;

when a microorganism is used that is neither a food grade microorganism nor a lactic acid bacterium, according to the invention essentially more than 60%, preferably more than 75% of the carbon consumed from the medium is converted into alanine.

Furthermore, the microorganism used is preferably essentially homo fermentative.

In particular, according to the invention the native metabolic conversion or conversions of pyruvate (derived from the conversion of glucose or another suitable source of sugar in the medium) is/are diverted to alanine formation, in such a manner that essentially more than 20%, preferably more than 40%, more preferably more than 60% and most preferably more than 75% of the pyruvate formed being converted into alanine, on the basis of carbon in the pyruvate formed:

when in the process of the invention a lactic acid bacterium is used (including the preferably applied food grade lactic acid bacteria), according to the invention essentially more than 20%, preferably more than 40%, more preferably more than 60% and most preferably more than 75% of the pyruvate formed is converted into alanine;

when a food grade microorganism is used that does not belong to the lactic acid bacteria, according to the invention essentially more than 40%, preferably more than 60% and more preferably more than 75% of the pyruvate formed is converted into alanine;

when a microorganism is used that is neither a food grade microorganism nor a lactic acid bacterium, according to the invention essentially more than 60%, preferably more than 75% of the pyruvate formed is converted into alanine.

The process provides alanine to a high degree of purity and in a high yield, and with an appreciably greater efficiency of carbon utilization in comparison with known processes. In this process it is possible to obtain a re-routing of more than 80% and even more than 90% of the carbon introduced as sugar source into alanine, or even an essentially complete diversion (>99%).

The invention also provides, in a preferred embodiment, an improved stereospecificity for L-alanine in the end product, it being possible for a stereo-specificity of over 95% or even 99% or more to be achieved.

The invention further provides, in a special embodiment, a suitable technique for the in-situ preparation of alanine during the preparation of fermented foodstuffs or food preparations.

The carbon source used may be any metabolizable or fermentable carbon source whose native metabolism can be diverted to alanine formation, as described herein. This will generally be a carbon source that the microorganism natively converts into pyruvate, inter alia via glycolysis-based reactions. The carbon source is generally a conventional metabolizable and fermentable sugar source such as glucose, lactose (for lactic acid bacteria, see de Vos and Simons in "Genetics and Biotechnology of Lactic Acid Bacteria", Gasson and de Vos eds., pp. 52–106, Chapman and Hall, 1994), sucrose (for lactic acid bacteria, see Rauch and de Vos, 1992a, J. Bacteriol. 174: 1280–1287 and Rauch and de Vos, 1992b, Gene, 121: 55–61), maltose or starch (for lactic acid bacteria, see Asseldonk et al., 1993, Mol. Gen. Genet., 240: 428–434). Glucose, lactose and sucrose are generally preferred.

The degree of diversion of the sugar metabolism to alanine formation is expressed according to the invention on the basis of carbon (the carbon balance), as is customary in this field, i.e. as [the amount of carbon (atoms) in the alanine formed]/[the amount of carbon (atoms) in the sugar source consumed]×100%.

The amount of alanine formed (in grams or moles) per gram or mole of sugar consumed will depend on (the number of carbon atoms in) the sugar source. Therefore, on the basis of 100% conversion, 1 mol of glucose will give 2 mol of alanine, whilst 1 mol of sucrose or lactose will give 4 mol of alanine.

The re-routing of the native sugar metabolism to alanine formation can be brought about by conferring an (increased) alanine-producing activity on the microorganism and preferably at the same time disrupting or suppressing the native conversion or conversions of pyruvate.

This (increased) alanine-producing activity can be conferred by bringing one or more homologous or heterologous genes coding for an alanine-forming activity in the microorganism to (increased) expression.

These genes will in particular be (one or more) structural genes coding for an enzyme, known per se, that catalyzes the formation of alanine, especially L-alanine, particularly an enzyme that can produce alanine from a fermentable sugar source in the medium, as described above, or a metabolite thereof.

The enzyme preferably used is one that is able to produce alanine by converting pyruvate into alanine, especially an alanine dehydrogenase. The structural gene that codes for this can be derived from any suitable microorganism but is preferably an alanine dehydrogenase from a lactic acid bacterium or from a bacterium of the Bacillis genus, especially *Bacillus sphaericus*. In particular, an alanine dehydrogenase derived from a food-grade microorganism will be used. It is also possible to use the alanine dehydrogenase that is endogenous to the microorganism and which is, if required, brought to over-expression for this purpose by prior induction and/or under the control of a suitable homologous or heterologous promoter.

As an example of an alanine-dehydrogenase (gene) from a microorganism that does not belong to the food grade microorganisms or lactic acid bacteria, the L-alanine dehydrogenase from Arthrobacter can be mentioned, of which the cloning is described in EP 0 603 865.

The native conversion or conversions of the pyruvate metabolism can be suppressed by inhibiting or blocking the corresponding metabolic route, for example through the presence in the medium of reversibly or irreversibly inhibiting factors for the enzymes involved in this route, or by disrupting and/or suppressing the native expression of these enzymes.

However, it is preferred to use microorganisms that have been genetically manipulated in such a manner that they are deficient in the native conversion or conversions of pyruvate, for example because they express the corresponding enzymes in a greatly reduced or defective way or not at all, such mutants being well known to the experts.

One example is the lactate-dehydrogenase-deficient strain of *L. lactis* described by Platteeuw et al., 1995, Appl. Environ. Microbiol., 61: 3967–3971. In this article, the pyruvate metabolism of this strain is diverted to diacetyi production by the over-production of alfa-acetolactate synthetase (to the extent of approximately 80%, depending on the growth conditions). However, in this case other products are formed in addition to diacetyl, so that only a small portion of the carbon source consumed is converted into the required product (diacetyl), whilst the conversion carried out upsets the redox balance of the microorganism, which is a considerable disadvantage.

The microorganism used may also be any well-known microorganism, or a well-known mutant thereof, and both a homofermentative and a heterofermentative microorganism may be used.

Homofermentative microorganisms are understood to mean those which convert sugars via pyruvate essentially (i.e. to the extent of over 80%, calculated on the carbon balance) into a single metabolic product. This includes, for example, lactic acid bacteria such as *L. lactis* and *S. cremoris*, which convert pyruvate essentially completely into lactic acid/lactate. Reference is made to H. G. Schlegel: Allgemeine Microbiologie [General Microbiology], 5th ed., Thieme Verlag, 1981, especially pp. 255–295.

Other examples are Clostridia species such as *C. acidi-urici* and *C. cylindro-sporum*, and the homofermentative subspecies *C. formicoaceticum* and *C. thermo-aceticum*, which form acetate in a homofermentative manner from hydrogen equivalents (from substrate oxidation) and carbon dioxide according to the reaction scheme:

However, these Clostridia species are generally not food-grade microorganisms.

Heterofermentative microorganisms are understood to mean those which transform the pyruvate into a number of principal conversion products. In the broadest sense, they include all the microorganisms that according to the above definition are not classed with the homofermentative microorganisms.

According to the present invention, the use of a homofermentative microorganism will generally be much preferred because in this case, replacing the conversion of pyruvate into the principal product derived from it by the conversion to alanine will already lead to an alanine production in a very good yield. For this purpose, furthermore, only one native route of the pyruvate metabolism has to be diverted, suppressed and/or disrupted. However, the use of heterofermentative microorganisms, in the case of which one or more of the principal native conversions of pyruvate is/are diverted to alanine production, is also within the scope of the present invention.

There are also some "semi-homofermentative" microorganisms which are known and which produce $CO_2$ in addition to a single main product (organic molecule). Although these microorganisms cannot strictly be classified with the homofermentative organisms according to the above definition (formation of over 80% of a single metabolic product, determined on the basis of total carbon), they may be regarded according to the present invention as equivalents of purely homofermentative microorganisms whenever they produce over 80% of a single metabolic product, determined on the basis of the carbon balance, where $CO_2$ is ignored. Another reason for this is that, when the metabolism of such an organism is diverted according to the invention, the final culture medium will essentially contain only alanine as the principal product, because the $CO_2$ formed from the medium will be released into the surrounding air. However, the use of purely homofermentative organisms will still be preferred.

The microorganism used is preferably a lactic acid bacterium, such as *L. lactis, L. bulgaricus, L. acidophilus, L. helveticus, S. cremoris* or *S. thermophilus, Lactobacillus plantarum*, or another homofermentative microorganism that can utilize lactose, sucrose, glucose and/or pyruvate as substrate. For some applications, the use of food-grade microorganisms will be preferred.

The microorganism used is preferably deficient in activity or activities and/or enzymes that compete with the alanine-producing enzyme for the available substrate. For example, when the alanine-producing enzyme is an L-alanine dehydrogenase gene, the microorganism used is preferably one that is deficient in the enzyme lactate dehydrogenase, which can convert pyruvate—the substrate for L-alanine dehydrogenase—into lactate.

For the stereoselective production of L-alanine, the microorganism preferably used does not contain any appreciable alanine racemase activity either. For this, any native racemase activity can be suppressed in a known manner, for example by including in the medium some reversibly or irreversibly inhibiting factors, by disrupting and/or suppressing the native expression of the racemase activity, or by using microorganisms that have been genetically manipulated in such a manner that they express any native racemase activity in a greatly reduced or defective way or not at all. Such mutants will also be well known to the experts.

The one or more homologous or heterologous genes coding for the alanine-forming activity can be brought to (over-) expression in the microorganism used in a well-known manner, for example under the control of a conventional homologous or heterologous promoter that is active in the microorganism used.

For this purpose, the one or more structural genes are actively combined with the promoter, for example by introducing the coding gene in the right orientation and the right reading frame into a plasmid or another suitable vector, which already contains the promoter in question. The microorganism is then transformed in the usual way with the aid of the resulting recombinant DNA molecule, it being possible for the recombinant DNA to be either included in the bacterial genome or used as a separate plasmid in the cell. For all this, the well-known recombinant techniques, as described in Sambrook et al., "Molecular Cloning: A Laboratory Manual", 2nd edition., vols. 1–3, Cold Spring Harbor (1989) may be used.

In principle, any suitable constitutive or inducible promoter that is active in the microorganism used may be used for this purpose. Examples of suitable constitutive promoters are the usp45 promoter (van Asseldonk et al., 1990, Gene, 95: 155–160), the nisR promoter (de Ruyter et al., 1997, J. Bacteriol., 178: 3434–3439), the pepN promoter (Tan et al., 1992, FEBS Lett., 306: 9–16) and the promoters mentioned in de Vos and Simons in "Genetics and Biotechnology of Lactic Acid Bacteria", Gasson and de Vos, eds., pp. 52–106, Chapman and Hall, 1994. Examples of suitable regulated promoters are the Ö31 middle promoter and ori-based expression system (O'Sullivan et al., 1996, Biotechnology, 14: 82–87), the xylA promoter (Lokman et al., 1994, Mol. Gen. Genet., 245: 117–125), and the repressor/operator Ö rlt system (Nauta et al., 1996, Mol. Microbiol., 19: 1331–1341).

The promoter used is preferably such that the alanine-producing activity can be brought to increased expression and more preferably to regulated over-expression.

A highly suitable class of promoters—auto-inducible promoters as described in, for example, Kuipers et al., TIBTECH, 15: 135–140—will be described below.

An important alternative to the use of independently replicating recombinant structural units (plasmids) that code for alanine dehydrogenase is the insertion of the alanine dehydrogenase gene into the chromosomal DNA of the microorganism used. This can be done in a well-known way, for example by using suitable phage vectors, F-factor plasmids or transposons, or by conjugation with a suitable donor strain. Examples are the nisin sucrose conjugative transposon Tn5276 (Rauch and de Vos, J. Bacteriol., 174:

1280–1287), transposon Tn919 (Hill et al., 1985, FEMS Microbiol. Lett., 30: 115–119) and pGHOST integrative vectors (Magiun et al., 1992, J. Bacteriol., 174: 5633–5638).

The alanine dehydrogenase gene involved here is generally brought to expression under the control of an endogenous promoter in the bacterial DNA, although chromosomal insertion of the alanine dehydrogenase gene, combined with a suitable homologous or heterologous promoter (such as the promoters mentioned above) is also possible.

According to a particular embodiment of the invention, the structural gene coding for the native enzyme which can compete with the alanine dehydrogenase gene for the substrate (pyruvate), such as the gene coding for lactate dehydrogenase in lactic acid bacteria, is replaced in the chromosomal DNA by the alanine dehydrogenase gene, which can, if required, be brought under the control of the native promoter for the replaced gene.

The microorganisms transformed in this way, which can bring an alanine-producing activity to increased expression—in comparison with the original/native microorganism—and which are at the same time preferably deficient in any competing native metabolism, especially in the native pyruvate metabolism, form another aspect of the invention.

The microorganism is then cultured under conditions ensuring the induction of the promoter and therefore the expression of the coding gene, after which the enzyme expressed is made to produce alanine from the constituents of the culture medium or its metabolites, especially glucose or another suitable fermentable carbon/sugar source. The culture medium can also contain all the conventional constituents of culture media, such as a suitable nitrogen source, together with trace elements and the like.

When the alanine-producing enzyme is an L-alanine dehydrogenase, the culture medium contains a source of ammonium ions in addition to a metabolizable carbon source or another pyruvate source. Ammonium ions are preferably present in the medium in a ratio of carbon source to ammonium ions of at least 1:3, calculated on the carbon consumed. In the case of glucose as the carbon source, for example, the ratio of glucose to ammonium is at least 1:2, while in the case of sucrose or lactose as the carbon source this ratio will be at least 1:4.

The expression of the alanine-producing enzyme and the formation of L-alanine can be controlled separately by the addition of the inducing factor for the promoter and the substrate for the alanine-producing enzyme, respectively. In this case, the expression and the L-alanine production can be induced/obtained either simultaneously or successively, as described in detail below.

The level of expression of the alanine dehydrogenase is not very important in itself, provided that enough alanine is produced. This will generally depend on the microorganism used. For example, after the suppression/disruption of the natively competing routes, the endogenous alanine-forming activity present in the microorganism used may already be sufficient to produce enough alanine. When homologous or heterologous alanine dehydrogenase is brought to intensified expression, this enzyme can constitute up to 30–40% or more of the cellular protein.

The formation of L-alanine can, furthermore, be carried out in a well-known manner by using conventional microbiological techniques and reactors for culturing/treating the microorganism used or processes similar to these. For example, batchwise or continuous processes can be used.

It is also possible according to the invention to use the microorganisms in an immobilized form on a suitable carrier, for example in an appropriate cell reactor or in a column.

However, the use of intact cells of the microorganism will generally be preferred according to the invention over the use of cell extracts such as cell-free extracts.

The alanine formed can then be isolated from the fermentation medium and possibly purified further by a conventional method.

The process according to the invention gives alanine to a high degree of purity (>90%, preferably >99%), the efficiency of glucose consumption also being high (>75%). Especially when any native racemase activity present is suppressed as described above, the process also gives a high level of stereo-specificity, an end product being obtained that contains more than 80%, especially more than 95% or even 100% of the L-isomer (calculated on the total amount of alanine) (total stereospecific production).

In further aspects, the invention relates to the alanine obtained according to the process described here, together with preparations, especially foodstuffs and/or health-promoting preparations, as well as additives therefor, which contain alanine produced according to the process. Furthermore, the invention may also be used for the large-scale production of the alanine-producing enzyme, as described above.

Finally, in a further aspect the invention relates to a very convenient system for controlling the expression of the alanine-producing activity, especially when the process according to the invention is carried out in lactic acid bacteria.

This aspect comprises the use of an "auto-inducible" promoter, which is understood to mean one that can be induced by the expression product of the coding gene which is natively controlled by this promoter, including any post-translation modified expression product, as well as analogues and derivatives of such expression products.

This aspect of the invention therefore relates to a process for preparing alanine, especially L-alanine, by culturing an alanine-producing genetically modified microorganism, in which the microorganism used is one that contains a gene coding for an alanine-producing enzyme under the control of an auto-inducible promoter that is active in the microorganism, this promoter being derived from a gene cluster that codes for an antimicrobial peptide or a similar signal protein.

According to this aspect, auto-inducible promoters that natively control the expression of gene clusters which code for antimicrobial peptides are used in particular. Such promoters can be induced by the antimicrobial protein itself, as well as by its analogues and derivatives, generally via a two-component signal transduction system.

Non-limiting examples are the promoters from the bacteriocin gene cluster of *Carnobacterium piscicola,* the Sakaricin gene cluster from *Lactobacillus sake,* as well as (presumably) the Subtilin gene cluster from *Bacillus subtilis.* According to the invention these also include promoters for similar, non-bactericidal signal proteins involved in the quorum sensing process in microorganisms, such as the promoter for Plantaricin A from the bacteriocin gene cluster of *Lactobacillus plantarum.* Reference is made to Kleerebezem et at., Molecular Microbiology (1997) 24 (5), 895–904 and the references mentioned therein.

The preferred promoters used are the auto-inducible promoters from the nisin gene cluster of *L. lactis,* especially the nisA and nisF promoters, as described in the Applicant's European Application 0,712,935 (nis A) and also in De Ruyter et al., Appl. Environ. Microbiol., 62: 3662–3667 (1996); Kuipers et al., Tibtech, April 1997 (Vol. 15): 135–140, and the references given therein (nisA and nisF).

These promoters have already been used for the controlled (over-) expression of homologous and heterologous proteins (such as the gusA reporter gene from E.coli, pepN, and the lytic genes lytH and lytA) in lactic acid bacteria and for the nisin-induced expression in heterologous hosts such as Lactobacillus helveticus and Leuconostoc lactis. According to the invention, this auto-inducible promoter system is advantageously used for the controlled (over-) expression of the alanine-producing activity, i.e. of the alanine-producing enzyme.

The gene that codes for the alanine dehydrogenase can be brought under the control of the nisin promoter in the manner described above by being actively combined with this promoter. For example, the coding gene can be introduced, in the correct reading frame, into a plasmid or vector that already contains an auto-inducible promoter, essentially in a similar way to the processes described in EP-A-0,712,935 and in the paper by De Ruyter et al. mentioned above.

Therefore, a further aspect of the invention relates to recombinant DNA molecules or sequences that comprise one or more genes coding for an alanine-producing activity, especially for an alanine-producing enzyme, such as L-alanine dehydrogenase that has been brought under the control of an auto-inducible promoter, especially a promoter from the nisin gene cluster as described above.

The recombinant DNA molecule is preferably in the form of a vector, such as a plasmid, which can at the same time also contain selectable markers and other well-known vector components. The preferred plasmids used are described below in more detail.

The microorganisms can be transformed with these vectors according to the invention in a well-known manner, for example as described in EP-A-0,712,935 and in the paper by De Ruyter et al. mentioned above.

The microorganisms transformed in this way—which constitute a further aspect of the invention—can be used for the production of L-alanine by being cultured in a medium that contains at least one inducing factor for the auto-inducible promoter in an inducing concentration. This ensures the expression of the alanine-producing activity, which can then be used for forming L-alanine from a suitable substrate that can be included in the medium.

Suitable inducing factors are notably (but not necessarily) the expression products of the gene/genes that is/are natively controlled by the promoter used, as well as analogues and derivatives thereof. They are generally antimicrobial proteins or similar "peptide pheromones", such as—for the nis promoters—nisin A, nisin Z and analogues/derivatives thereof, as well as mutants, variants and/or fragments thereof.

The induction can also be carried out as described in EP-A-0,712,935 and in the above paper by De Ruyter et al., or in a similar way. This preferably ensures increased expression or over-expression of the desired L-alanine-producing activity in comparison with the native microorganism.

When an auto-inducible promoter is used, the cells of the microorganism used preferably contain (the genes for) a signal transduction system, which induces the promoter in response to the inducing factor present outside the cell. This system will often consist of two components (i.e. a sensor protein and a response regulator) as in the known nisK and nisR genes/proteins from the nisin gene cluster. This signal transduction system may even be present natively in the microorganism used, or be conferred on the microorganism by a suitable expression of heterologous genes. The preferred signal transduction system used is one that is natively involved in the control of the promoter used. Reference is made to the above paper by Kleerebezem et al. and the references mentioned therein.

The use of the auto-inducible promoter system according to the invention further ensures all the well-known advantages of this system, as described in EP-A-0,712,935. For example, it is possible to induce the expression of the alanine-producing activity at any desired moment during the fermentation and this expression varies essentially linearly with the concentration of the inducing factor in the medium (positive induction).

Furthermore, the preferred inducing factors used (nisin A, nisin Z and their analogues/derivatives) are acceptable for use in foodstuffs, because they are formed natively in the fermentation of dairy products by lactic acid bacteria. As a result, the invention may also be advantageously used in situ for preparing preferably fermented foodstuffs, for example for the controlled in-situ production of alanine as a sweetener in dairy products, especially in cheese or in fermented dairy products such as yoghurt. A further advantage here is that the alanine production can be induced without having to make any substantial changes to the nutrient (medium).

In this case, the microorganism can be used in combination with the common acidifying microorganisms, it being possible for the microorganisms according to the invention also to be derived from these common acidifying gents.

BRIEF DESCRIPTION OF THE DRAWINGS

The invention will now be explained with reference to the following non-limiting examples and figures, wherein.

EXPERIMENTAL SECTION

Lactic acid bacteria are involved in various processes used in the production of food by fermentation. For example, L. lactis is directly involved in the production of dairy products such as Gouda cheese or buttermilk. L. lactis causes a homolactic fermentation, in which lactate is formed as the principal end product from glucose.

According to the invention, this native metabolic route (from pyruvate to lactate) is preferably diverted from pyruvate to alanine. For this purpose, an L-alanine dehydrogenase gene is brought to expression in a—preferably—wild type of lactic acid bacterium or in a mutant thereof that is deficient in lactase hydrogenase.

The enzymatic conversion of pyruvate into alanine proceeds according to the following reaction scheme:

pyruvate+$NH_4^+$+NADH . . . >L-alanine+$H_2O$+$NAD^+$.

When an L. lactis strain deficient in lactate dehydrogenase is used, alanine will be produced from glucose predominantly and preferably essentially exclusively—with an appropriate control of the pH as described below. In the absence of any pH control, a mixture of acetoin and alanine will be formed. In both cases, the native glucose metabolism will be diverted to the extent of 50 to 60%. When a wild strain of L. lactis is used, a mixture of lactate and alanine will be obtained from glucose, the metabolism being diverted to the extent of 30 to 40%.

The production of alanine by these microorganisms can be conducted as a continuous or batchwise process. In a batchwise process, the use of cell suspensions of L. lactis in a suitable buffer may give an essentially full conversion of glucose to alanine (18 g/l) (homoalanine fermentation), the alanine obtained being about 99.5% pure

EXAMPLE I
Over-expression of the L-alanine Dehydrogenase Gene From *Bacillus sphaericus* (alaD) in a Wild and an LDH-deficient Strain of *L. lactis*

The nisin-inducible over-expression system described by De Ruyter et al. was used for the expression of the alaD gene.

Figure 1:
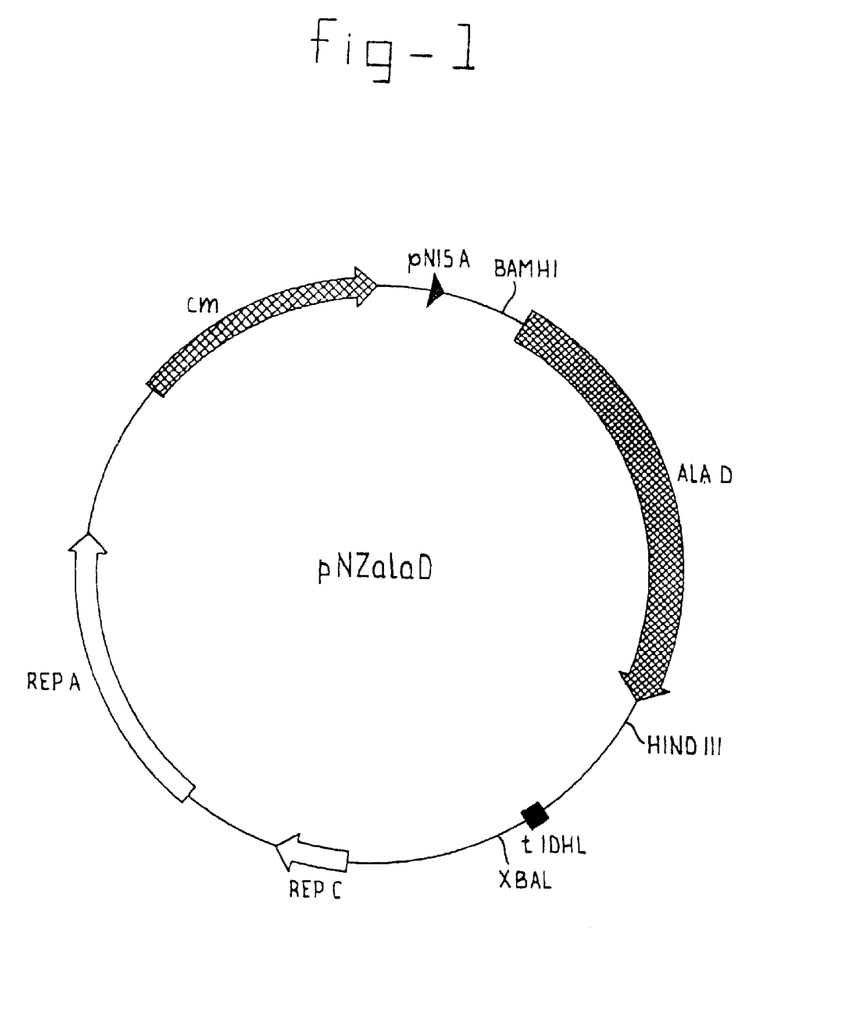
FIG. 1 is a chart for the plasmid pNZalaD.

For this purpose, the alaD gene in plasmid pNZ8020 was actively combined with the nisA promoter, giving the plasmid pNZalaD (FIG. 1). This plasmid was transferred into the NZ3900 strain, which contains the necessary regulating elements nisRK, integrated in the pepN locus. Both the plasmid pNZ8020 and the NZ3900 strain are described by de Ruyter et al.

Figure 2:
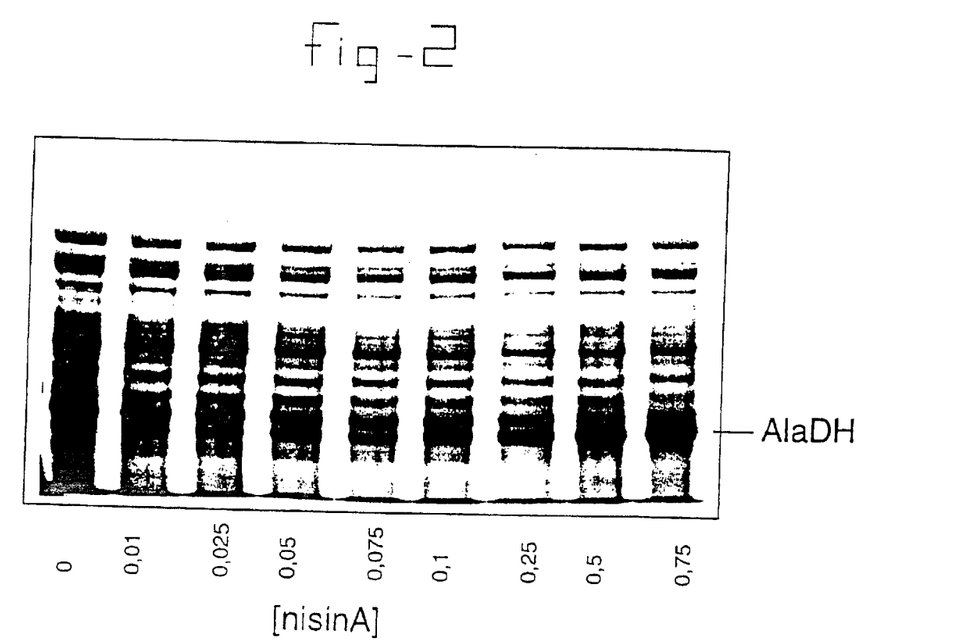
FIG. 2 shows a gel obtained by electrophoresis in SDS-PAGE (10%) (10 ig of total protein per sample), which illustrates the (over-) production of AlaDH in NZ3900/ LDH$^-$[pNZalaD] at various nisin concentrations in the medium (given by the numbers along the horizontal axis)

At the same time, an isogenous LDH-deficient strain was constructed by a simple cross-over with the plasmid pNZ2007 (described by 61: 3967–3971 (1995)) Platteeuw et al., Appl. Environ. Microbiol. This LDH-deficient strain was then transformed with the aid of the plasmid pNZalaD. Two isogenous strains gave an over-expression of the alanine dehydrogenase, a linear dose/response relationship between the L-alanine dehydrogenase production and the nisin concentration in the medium being obtained. The highest over-expression of LDH, corresponding to about 40% of the total protein produced, was obtained at a concentration of 0.75 ng of nisin A per ml of medium (FIG. 2).

EXAMPLE II
Alanine Production in the LDH-positive NZ3900[pNZalaD] Strain

A two-stage procedure was developed to study the end products of the glucose fermentation.

In the first stage, the cells were charged with L-alanine dehydrogenase by induction with nisin A. In the second stage, the cells were collected, concentrated (to an $A_{600}$ value of 10) and resuspended in phosphate buffer (100 mM, pH 7.0) supplemented by glucose (100 mM) and a source of ammonium ions (100 mM). This suspension was incubated for 1 hour at 30° C. without pH control. The formation of the end products from glucose was monitored using HPLC analysis.

Figure 3A:
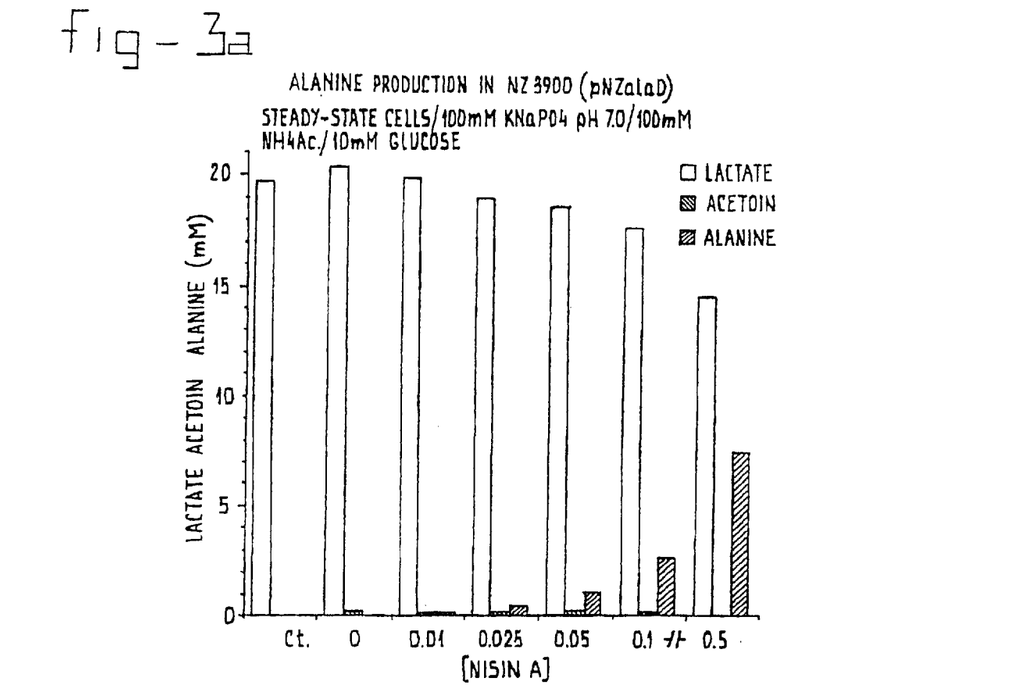
FIGS. 3A–3E show the effect on the alanine production in the case of conversion of 10 mM of glucose in small-scale cell suspensions of the nisin A concentration (FIG. 3A and FIG. 3B), ammonium acetate concentration (FIG. 3C), the ammonium source used (FIG. 3D) and the pH of the starting mixture (FIG. 3E).

This method was used to investigate the effect of the nisin A concentration, the ammonium concentration, the ammonium source used and the pH used. The results showed that the alanine production was directly related to the amount of nisin A that was introduced during the charging of the cells with alanine dehydrogenase (FIG. 3A). At the highest induction, the end products, from glucose, are a mixture of lactate and alanine, with a 30% diversion of the native glucose metabolism (Table 1).

Figure 3B:
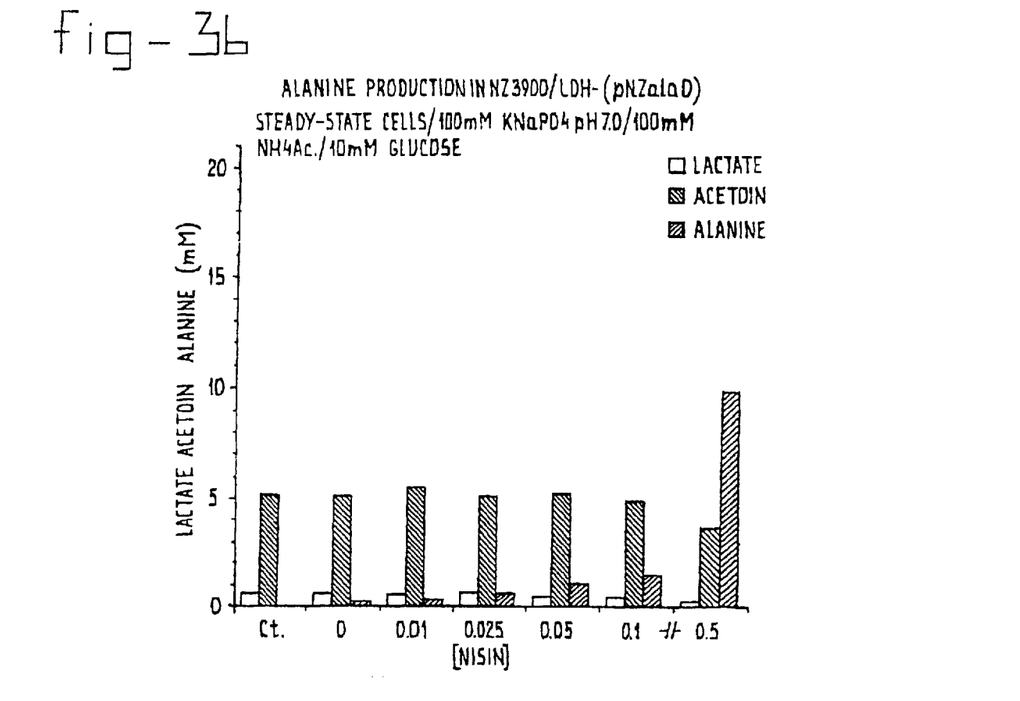
Figure 3C:
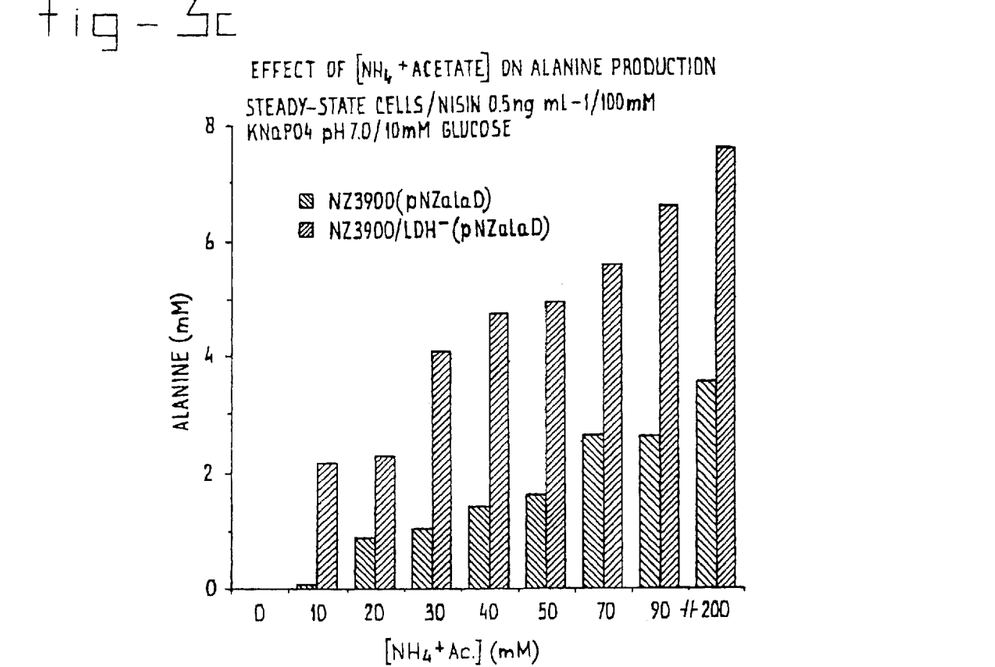

At a constant nisin concentration, the amount of alanine produced is related to the extracellular ammonium concentration (in the progression from 0 to 200 mM of ammonium acetate, see FIG. 3C). Furthermore, the ammonium source used (ammonium acetate, ammonium sulphate or ammonium chloride) has a great influence on the final alanine concentration (see FIG. 3D). Ammonium acetate is therefore preferably used.

Figure 3D:
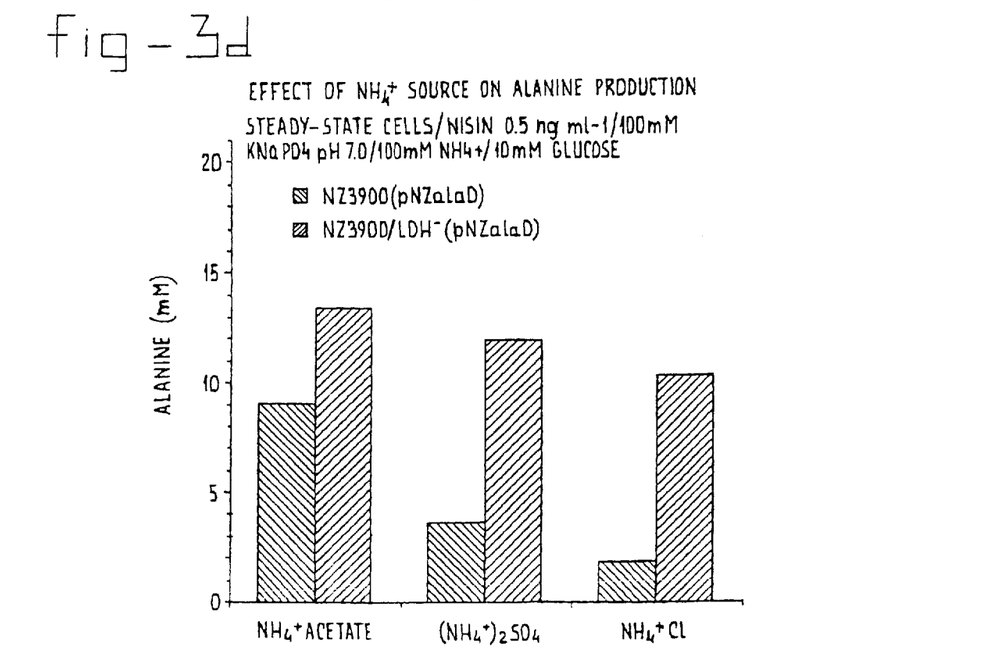
Figure 3E:
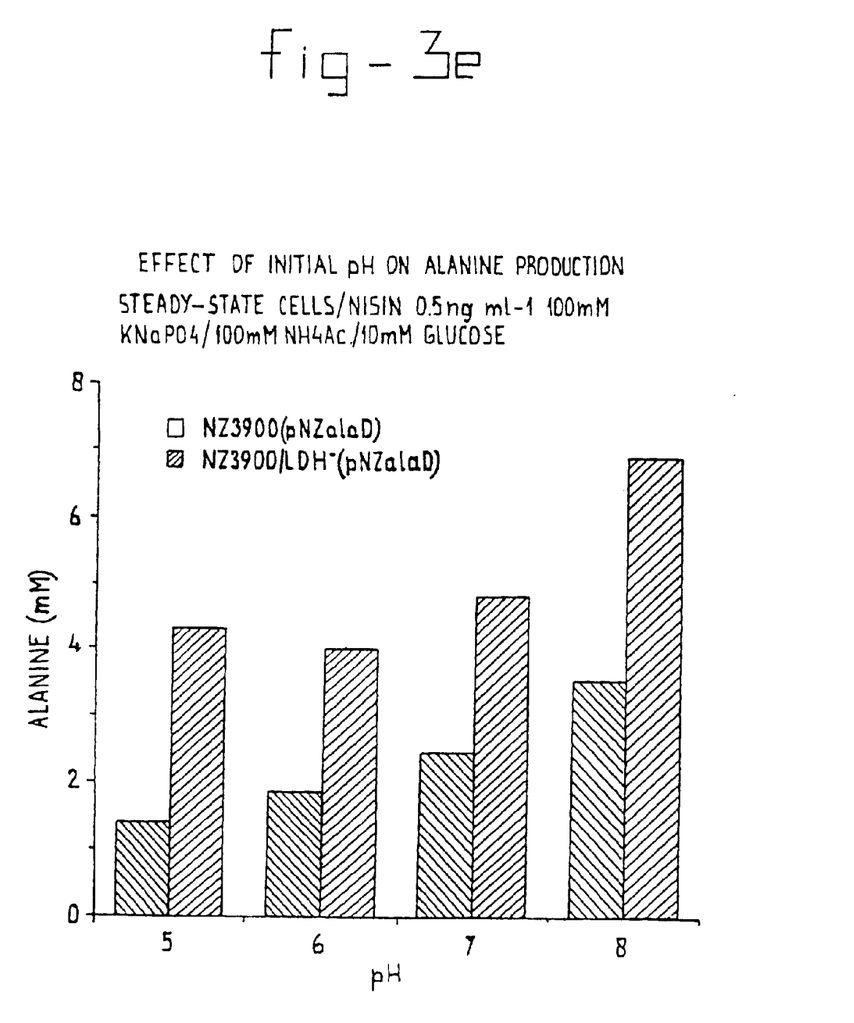

Finally, the alanine production is affected by the pH of the medium, especially the pH of the initial mixture (in the range from pH 5 to 8, see FIG. 3E). The highest production is obtained with an initial pH of 8 (corresponding to an internal pH of about 8.5), which lies in the optimum pH range for the enzyme used (between 8.5 and 9).

Figure 4A:
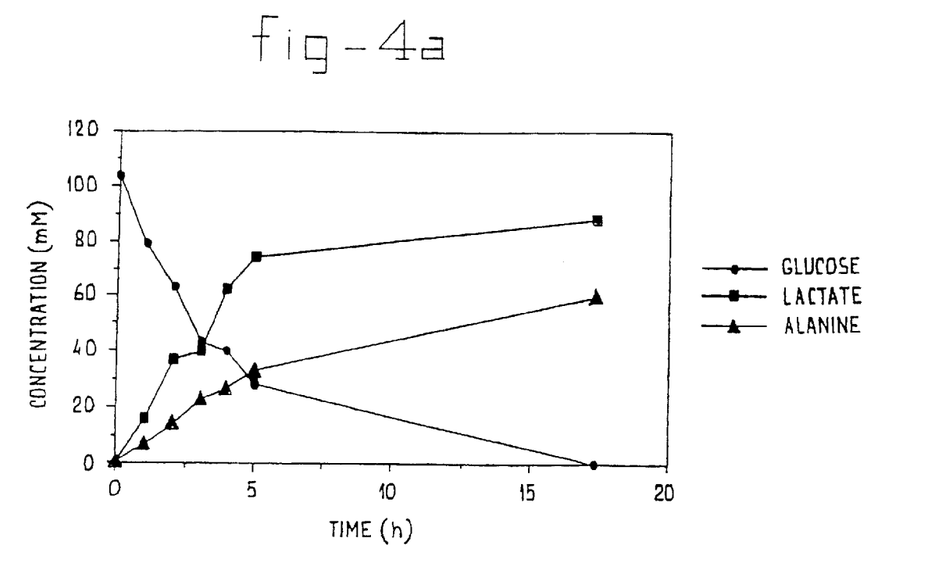
FIG. 4 shows the variation of glucose consumption and alanine and lactate production over time in cell suspensions supplemented by 100 mM glucose and 100 mM ammonium sulphate (pH kept at 7.5 with the aid of NaOH) in the case of pNZ3900(pNZalaD) (FIG. 4A) and NZ3900/LDH$^-$ (pNZalaD) (FIG. 4B).

The above procedure was repeated, the pH being adjusted to 7.5 and kept constant by the addition of NaOH. The initial glucose and ammonium sulphate concentrations were both adjusted to 100 mM. FIG. 4A shows the production over time of the most important starting materials and products (glucose, alanine and lactate). The fermentation with pNZ3900[pNZalaD] ends after 11 hours and gives lactate (88.6 mM), alanine (60 mM) and acetate (8 mM), the degree of diversion of the native metabolism to alanine being 36%.

EXAMPLE III
Alanine Production in the LDH-deficient Strain NZ3900/LDH⁻[pNZalaD]

The two-stage procedure of Example II was used to investigate the alanine production in an LDH-deficient strain.

The effect of the nisin A concentration, the ammonium concentration, the ammonium source used and the pH of the starting mixture was investigated essentially as described in Example II for the LDH-positive strain.

Alanine production is directly related to the amount of nisin A in the medium during the charging of the cells with alanine dehydrogenase (FIG. 3B). At the highest induction, the end products obtained from glucose are mainly a mixture of acetoin and alanine, corresponding to a 50% diversion of the metabolism (Table 1).

At a constant nisin concentration, the amount of alanine produced is again related to the extracellular ammonium concentration (over the range from 0 to 200 mM of ammonium acetate, FIG. 3C), but a lower ammonium ion concentration is needed than in the case of the LDH-positive strain for the alanine production. Furthermore, the ammonium source used (ammonium acetate, ammonium sulphate or ammonium chloride) and the pH of the starting mixture have less influence on the final alanine concentration than in the case of the wild strain (FIGS. 3D and 3E). The highest alanine production is again achieved with a pH of 8 for the starting mixture.

Figure 4B:
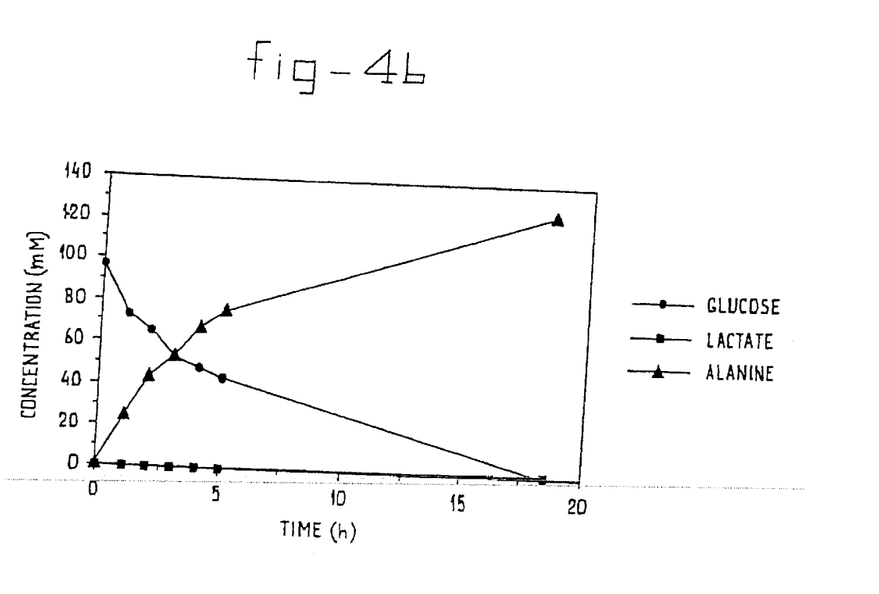

The pH control seems to be fairly important for the alanine production by the microorganisms described here. A similar procedure to that described in Example II was used, the pH being kept at 7.5. The initial glucose and ammonium sulphate concentrations were both kept at 100 mM. FIG. 4B shows the variation of the main starting materials and products (glucose, alanine and lactate) over time. The fermentation with NZ3900/LDH⁻[pNZalaD] ends after 17 hours and results in mainly alanine production, corresponding to an 80% diversion of the metabolism. Further fermentations were conducted with higher ammonium sulphate concentrations, because 100 mM ammonium sulphate might be a limiting factor. For example, 200 mM of ammonium ions would be needed for the complete conversion of 100 mM of glucose into 200 mM of alanine.

Figure 5:
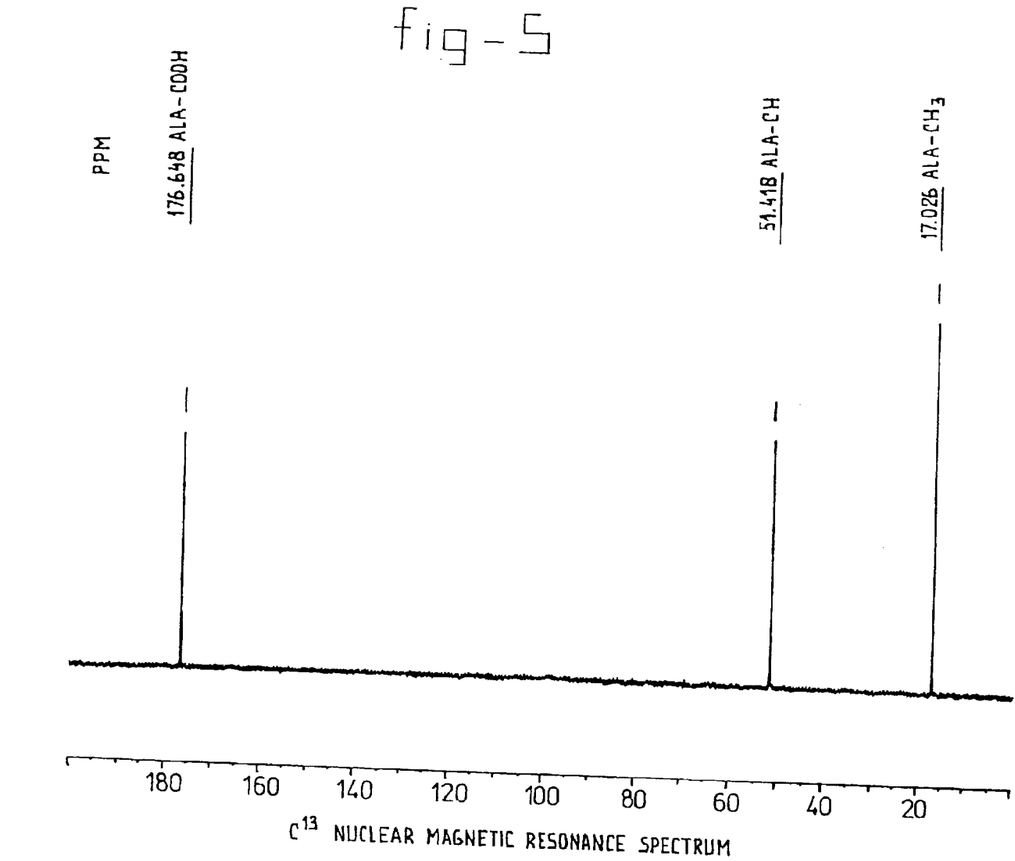
FIG. 5 shows an NMR spectrum of the end products obtained after 17 hours from a cell suspension (pH 7.5) of NZ3900/LDH$^-$(pNZalaD), supplemented by 100 mM glucose and 150 mM ammonium sulphate.

A fermentation was therefore carried out with 150 mM ammonium sulphate (corresponding to 300 mM of ammonium ions), a conversion of glucose (100 mM) to alanine (200 mM, 18 g/l) of essentially 100% being obtained. A sample taken after 17 hours of fermentation was analysed by $^{13}$C-NMR (FIG. 5), alanine being obtained as the only product, with a purity of almost 99.5%.

The (LDH−)NZ9300 strain, pNZalaD, was deposited at the Centraal Bureau voor de Schimmelcultures (CBS) in Baarn on Jan. 16, 1998.

EXAMPLE IV

Production of L-alanine Isomers in the Strains NZ3900/ALR⁻[pNZalaD] and NZ3900/LDH⁻/ALR⁻[pNZalaD].

The L-isomer of alanine is of greatest interest for practical purposes. However, L. lactis carries an alanine racemase activity. The production of both the L- and the D-isomer in the end product was observed in the case of the samples obtained in Examples II and III with the aid of enzymatic assays that are specific for each isomer. A mixture of the two isomers is obtained, in which the D-isomer amounts to about 10–15% of the end product. This racemization is the result of an enzymatic conversion, as the presence of specific inhibitors of alanine racemase activity during the alanine production, such as D-chloroalanine, leads to a considerable decrease in the amount of the D-isomer obtained (to below 3%). To prevent this racemization, the alanine racemase gene (alr) was disrupted by homologous recombination. For this purpose, a "suicide disruption vector" was constructed as follows. A PCR fragment with about 660 base pairs, corresponding to the internal fragment of the alr gene, was obtained by using the following two primers:

Primer 1:5'-CGAGGATCCGGCCGGTTGAG-
GTTTCTAAAGCGG-3'    SEQ. ID NO:1

Primer 2:5'-CGCGAGCTCACTTGTTTCATAAGTTG-
CACCGTAACC-3'    SEQ ID NO:2

This PCR fragment was then cleaved with BamHI and SstI and inserted at the corresponding restriction sites of the suicide plasmid pJDC9 (Chen and Morrison, Gene, 64: 155–165 (1988)). The alanine racemase-negative strains of NZ3900[pNZalaD] and NZ3900/LDH[pNZalaD] were obtained and investigated for the production of only L-alanine, essentially by the procedures of Examples II and III. Both deficient strains produced substantially only the L-isomer of alanine according to the enzymatic assays used in Examples II and III.

EXAMPLE V

Alanine Production from Lactobacillus plantarum NC8

The nisin-inducible system was transferred in L.plantarum NC8 (plasmid-free strain) [Aukrust, T. et al. (1992) Food Res.Int. 25:253–261] as follows. The necessary regulatory genes nisRK were integrated in the chromosome at the tRNA$_{ser}$ locus by site-specific recombination using the integration system of phage MV4 (pMC1 derivative) [Dupont, L., et al. J.Bacteriol. 177 : 586–595]. The recombinant strain was further transformed with plasmid pNZalaD.

A similar two-step procedure developed for Lactococcus lactis was used to evaluate alanine production. The cells were pre-loaded with dehydrogenase using various concentrations of nisin A (0, 5, 10, 25, 50 ng ml⁻¹) and concentrated to A$_{600nm}$=10. The small-scale cell suspensions (4 ml) made use of a KNaPO4 buffer (100 mM, pH 7.5) supplemented with glucose (50 mM) and ammonium sulphate (100 mM). The suspensions were incubated for 90 min without pH control.

Figure 6A:
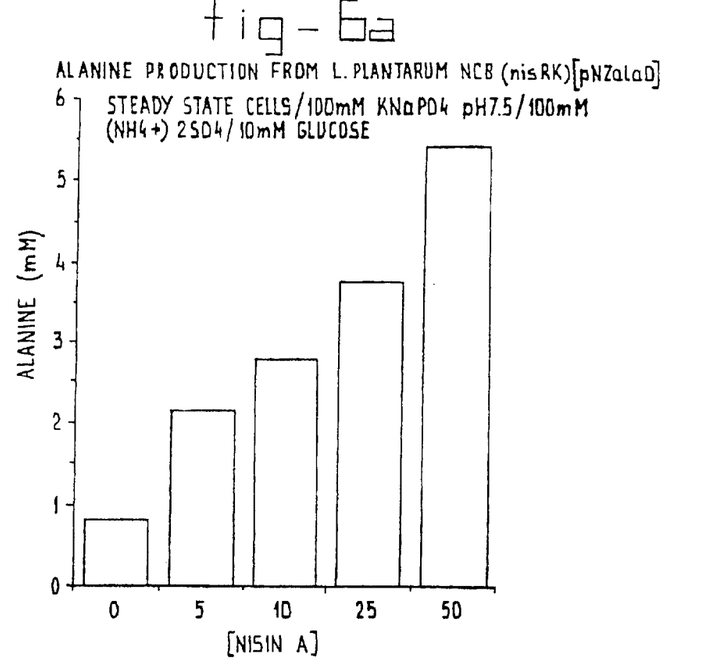
FIGS. 6A–6B show the influence of nisin A concentration in the medium on the amount of alanine formed in total in two separate experiments (FIG. 6A and FIG. 6B)
Figure 6B:
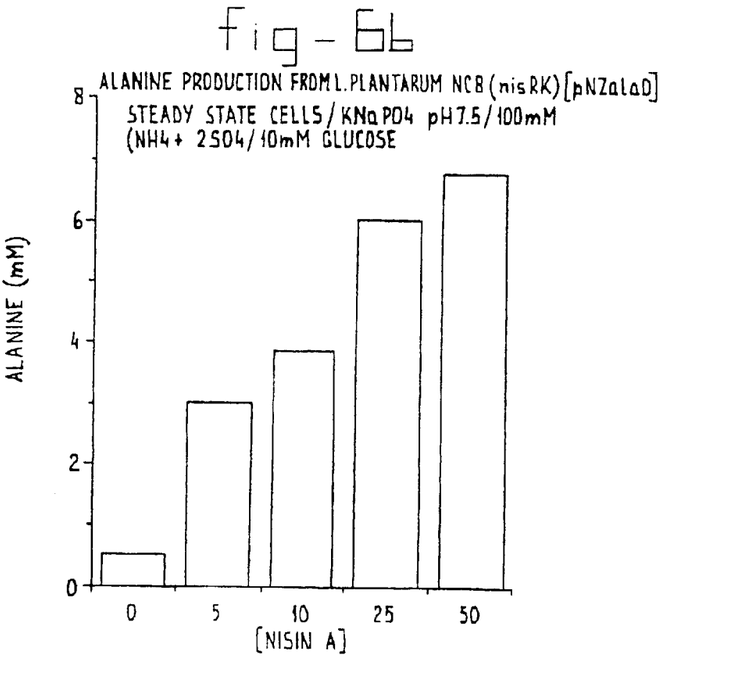

The production of alanine is directly related to the amount of nisin A added during the pre-loading of the cells with alanine dehydrogenase (FIG. 6A and 6B). At maximum induction (50 ng nisin A ml⁻¹), the end-products from glucose are a mixture of alanine and lactate with a re-routing comprised between 25% (FIG. 6A) and 33% (FIG. 6B) (Table 2). This re-routing is similar to the data obtained for the LDH-positive strain of L.lactis (NZ3900) harbouring pNZalaD.

Figure 6C:
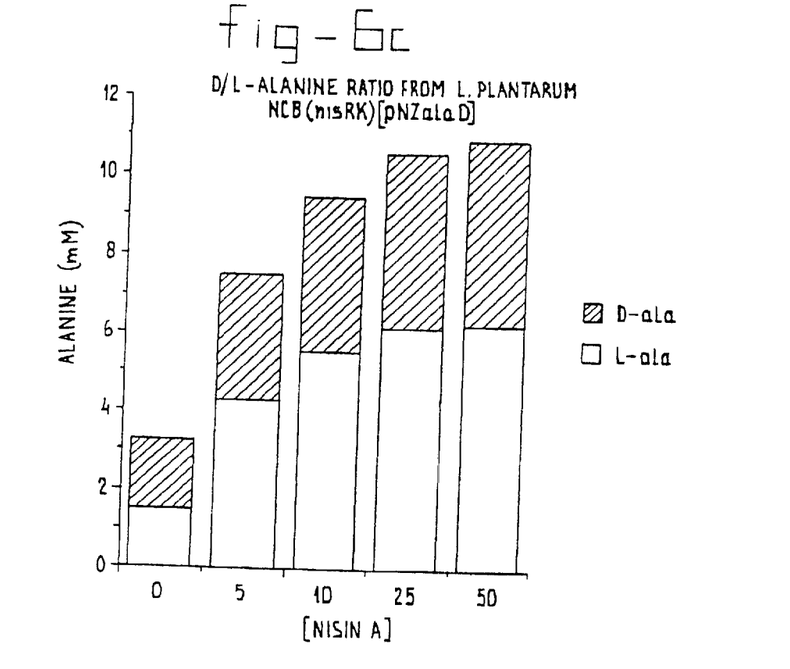
FIG. 6C shows the ratio of the amount of D-alanine and L-alanine isomer formed in the experiment of FIG. 6A (FIG. 6C)
Figure 6D:
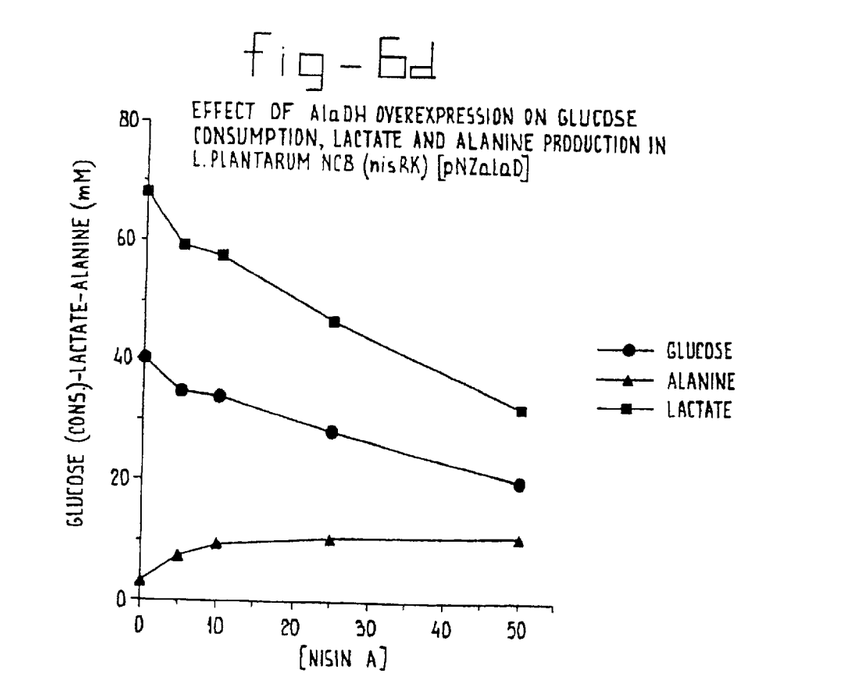
FIG. 6D shows the influence of the nisin concentration in the medium on the concentration of glucose, lactose and alanine in the medium.

Both isomers of alanine were quantified by enzymatic assays and the D-alanine isomer in this case accounts for 40% of total alanine (FIG. 6C) (Table 2).

TABLE 2

Product formation (mM) from glucose (10 mM) with cell suspensions of L. plantarum NC8 (nisRK) [pNZalaD] in KNaPO$_4$ buffer (100 mM, pH 7.5) supplemented with (NH$_4$⁺)$_2$SO$_4$ (100 mM) + 50 ng ml⁻¹ nisine A

| Strain | Glucose | L-alanine | D-alanine | L + D-alanine | L-lactate | D-lactate | L + D-lactate |
|---|---|---|---|---|---|---|---|
| NC8 (nisRK) [pNZalaD]6A | 10 | 3.1 | 2.3 | 5.4 | 7.5 | 8.2 | 15.7 |
| NC8 (nisRK) [pNZalaD]6B | 20 | 4.2 | 2.6 | 6.8 | 7.2 | 6.5 | 13.7 |

EXAMPLE VI

Production of Alanine in Lactobacillus plantarum

Similar to the example described above the nisRK genes were introduced into tRNA$_{ser}$ locus of a ldhD and ldhL deficient Lactobacillus plantarum strain; TF103 (Ferain, T., et al., (1996), J.Bacteriol. 178: 5431–5437). The resulting strain was transformed with plasmid pNZalaD.

Alanine production experiments were carried out according to the same procedures as described for the LDH-positive Lactobacillus plantarum strain. The production of alanine in the second stage of the experiment was directly related to the amount of nisin A added during the first or pre-loading stage. At maximum induction, the end-product from glucose is mainly alanine in this strain and amounted to more than 80% of re-routing of the carbon flux.

Both isomers of alanine were identified and the D-alanine isomer accounted for approximately 40% of total alanine. With regard to the latter aspect it is expected that stereospecific alanine production could be reached in this strain by inactivation of the alanine racemase encoding gene of *Lactobacillus plantarum*, which has been shown to be possible in the LDH-positive strain NC8 when growth media are supplemented with D-alanine (Hols, P., et al. (1997), J. Bacteriol. 179: 3804–3807).

EXAMPLE VII
Production of L-alanine in Immobilised Cells

*Lactobacillus lactis* NZ3900/LDH⁻ [pNZalaD] (Example II) was cultured under maximum inducing conditions. The "loaded cells" thus obtained (containing relatively high amounts of the alanine dehydrogenase) were immobilised in Ca-alginate or κ-carrageen. By immobilisation a strict separation between microorganisms and fermentation liquid is realised, as a result of which the bio-reactor concept can be analysed under more practical conditions. The immobilised cells were incubated in bio-reactor buffer (100 mM phosphate buffer, pH 7.5) which contains 100 mM glucose and 150 mM ammonium sulphate. The reactor fluid produced was analysed during the first 24 hours and proved to contain as main product (>95%) alanine. The cells immobilised in κ-carrageen proved to be more stable under these conditions, which might be a result of the relatively high pH as a result of which the immobilisation in alginate might be more unstable. The levels of glucose consumption and related alanine production proved to be stable during the first 24 hours and showed hardly deviation from the corresponding conversion levels found in 'free cells'. The glucose consumption was calculated to be approximately 20 mM per hour.

EXAMPLE VIII
In-situ Production of Alanine

A *B. subtilis* alad gene is inserted into a lacF nisin promoter plasmid in such a way that the structural gene is brought under the control of the nisin promoter (nis A or nis F).

This plasmid is used for transforming a food-grade LDH deletion strain of *L. lactis* containing the nisRK signal transduction system, by a two-stage homologous recombination process. This gives a food-grade *L. lactis* strain (LDH⁺ or LDH⁻), which brings the *B. subtilis* alaD gene to expression under the control of the auto-inducible nis promoter.

Alternatively, the native region that codes for lactate dehydrogenase on the chromosomal DNA of the *L. lactis* strain was replaced by a sequence that codes for *B. subtilis* alaD, for example using well-known gene replacement techniques and a lacF selection marker in a lacF mutant strain, it also being possible to obtain an *L. lactis* strain with a food-grade expression of *B. subtilis* alaD.

The resulting alanine-producing *L. lactis* strains are used, possibly after an in-vito characterization, for preparing fermented dairy products, such as butter-milk. The alanine-producing strain will generally be used here as an adjunct starter in addition to the customary acidifying agents that are normally present in starter cultures for the fermentation of such products.

When according to the invention the alanine-producing strain is applied as an adjunct-starter generally the carbon metabolism of used strain will be re-routed mainly to the formation of alanine, meaning more than 60%, preferably more than 75%, in addition to which as the remainder mainly lactic acid/lactate will be produced.

When according to the invention an alanine-producing strain is applied as a main-starter generally this strain also will (have to) produce, besides the alanine, a substantial amount of lactic acid/lactate, According to the invention in such a lactic acid bacterium, to be applied as main-starter, it is possible that the carbon metabolism is re-routed to the formation of alanine for as little as 30%, or even for only 20%, in addition to which as the remainder mainly lactic acid/lactate will be produced.

During the fermentation, which is then conducted in a well-known manner, the alanine production is induced by the addition of a sub-inhibitory amount of nisin to the medium.

This gives a buttermilk with a high alanine content and so a sweeter taste than that of conventional buttermilk.

The alanine-producing *L. lactis* strains can also be used/investigated in a Gouda cheese model system (CH-EASY model), in which the amount of alanine formed in the fermented product and the taste and other characteristics of the cheese are determined as a function of factors such as the fermentation conditions and the nisin concentration in the medium.

What is claimed is:

1. A process for producing alanine, the process comprising the step of culturing a bacterium, wherein the bacterium is transformed with a vector comprising an endogenous or heterologous alanine dehydrogenase gene wherein expression of the alanine dehydrogenase gene in the vector causes a diversion of at least part of the native carbon metabolism of the bacterium to the formation of alanine, wherein the bacterium lacks lactate dehydrogenase activity.

2. A process according to claim 1, wherein the bacterium is a homofermentative bacterium.

3. A process according to claim 1, wherein the bacterium is a homofermentative bacterium and a lactic acid bacterium.

4. A process according to claim 1, wherein the bacterium is a lactic acid bacterium.

5. A process according to any one of claim 2, 3, or 4, wherein the bacterium lacks alanine racemase activity.

* * * * *